US006315751B1

(12) United States Patent
Cosgrove et al.

(10) Patent No.: US 6,315,751 B1
(45) Date of Patent: *Nov. 13, 2001

(54) CARDIOPULMONARY BYPASS SYSTEM USING VACUUM ASSISTED VENOUS DRAINAGE

(75) Inventors: Delos M. Cosgrove, Hunting Valley; Robert C. Foster, Rocky River, both of OH (US)

(73) Assignee: Cleveland Clinic Foundation, Cleveland, OH (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/911,870

(22) Filed: Aug. 15, 1997

(51) Int. Cl.$^7$ .......................... A61M 37/00; A61M 1/14; A61M 1/34; A61M 1/36

(52) U.S. Cl. ....................... 604/5.01; 604/4.01; 604/6.13; 604/6.14; 422/45

(58) Field of Search .................................. 604/4.01, 5.01, 604/6.01, 6.05, 6.06, 6.1, 6.11, 6.13, 6.14, 6.16; 422/45

(56) References Cited

U.S. PATENT DOCUMENTS

| 3,890,969 | 6/1975 | Fischel . |
| 4,182,739 | 1/1980 | Curtis . |
| 4,205,677 | 6/1980 | Curtis . |
| 4,553,532 | 11/1985 | Bohls . |

(List continued on next page.)

FOREIGN PATENT DOCUMENTS

| 4326886 A1 | 2/1995 | (DE) . |
| 0309642 A1 | 4/1989 | (EP) . |
| 0357338 A2 | 3/1990 | (EP) . |
| 0786261 | 7/1997 | (EP) . |
| 2 008 022 C1 | 2/1994 | (SU) . |
| 84/03838 | 10/1984 | (WO) . |

OTHER PUBLICATIONS

Hirose, et al., "Reduction of Perfusion Hemolysis by the Use of Atraumatic Low–Pressure Section", J Thoracic and Cardiovas Surg, vol. 47, No. 2, pp. 242–247, Feb. 1964.
Baxter Product Information Document (PID), "HSR4000 Venous Reservoir with Cardiotomy Autotransfusion Filter". Cardiac Surgery, Morphology, Diagnostic Criteria, Natural History, Techniques, Results and Indications. vol. 1, Second Edition: John W. Kirklin, M.D. and Brian G. Barratt–Boyes, K.B.E., M.B., Ch.M.

(List continued on next page.)

Primary Examiner—Angela D. Sykes
Assistant Examiner—Patricia M. Biano

(57) ABSTRACT

A cardiopulmonary by-pass system having a vacuum assisted venous drainage system including a hard-shelled venous reservoir which is closed to atmosphere. The reservoir having a blood inlet for supplying blood removed under negative pressure during operation of the cardiopulmonary by-pass system to the reservoir, a blood outlet for removing blood from the reservoir, and a vacuum inlet for supplying a vacuum to the reservoir. A vacuum supply is also included for providing a predetermined desired vacuum of approximately –70 to –25 mmHG from a house wall vacuum source to the venous reservoir via the vacuum inlet. A patient support unit is also provided for receiving blood from the reservoir blood outlet, treating and returning revitalized removed blood under positive pressure. A vacuum regulator subassembly is also provided for manually setting the predetermined desired vacuum. A valve subassembly is further provided for manually enabling and disabling a vacuum from being supplied to the reservoir. The valve subassembly additionally includes a check valve for automatically disabling a vacuum from being supplied to said reservoir.

4 Claims, 6 Drawing Sheets

U.S. PATENT DOCUMENTS

| | | |
|---|---|---|
| 4,599,093 | 7/1986 | Steg, Jr. . |
| 4,923,438 | 5/1990 | Vasconcellos et al. .................. 604/4 |
| 5,011,469 * | 4/1991 | Buckberg et al. ........................ 604/4 |
| 5,021,048 | 6/1991 | Buckholtz . |
| 5,024,613 | 6/1991 | Vasconcellos et al. . |
| 5,039,430 | 8/1991 | Corey, Jr. . |
| 5,078,677 | 1/1992 | Gentelia et al. . |
| 5,087,250 | 2/1992 | Lichte et al. ......................... 604/321 |
| 5,127,900 | 7/1992 | Schickling et al. . |
| 5,141,504 | 8/1992 | Herweck et al. .................... 604/317 |
| 5,158,533 * | 10/1992 | Strauss et al. ...................... 604/4.01 |
| 5,158,539 | 10/1992 | Kolff et al. . |
| 5,171,207 | 12/1992 | Whalen . |
| 5,378,227 | 1/1995 | O'Riordan et al. ...................... 604/4 |
| 5,423,780 | 6/1995 | Malette ................................ 604/317 |
| 5,613,937 | 3/1997 | Garrison et al. . |
| 5,814,004 * | 9/1998 | Tamari ................................ 604/4.01 |
| 5,823,986 | 10/1998 | Peterson .................................... 604/4 |
| 5,957,879 * | 9/1999 | Roberts et al. ..................... 604/4.01 |

OTHER PUBLICATIONS

Heart–Lung ByPass Principles and Techniques of Extracorporeal Circulation: Pierre M. Galletti, M.D., Ph.D. and Gerhard A. Brecher, M.D., Ph.D, (1962).

Reoperataive myocardial revascularization: Floyd D. Loop, M.D., Manuel J. Irarrazaval, M.D., Delos M. Cosgrove, M.D.,Paul C.Taylor, M.D., Laurence K. Groves, M.D., and Leonard A. Golding, M.D. C leveland Clinic Quarterly, vol. 45 No. 1, An Improved Technique for Autotransfusion of Shed Mediastinal blood: Delos M. Cosgrove, M.D., Daniel M. Amiot, C.C.P., and John J. Meserko, B.S., C.C.P., M.B.A. (1984).

Augmented Femoral Venous Return: Lynn Solomon, M.D., Francis P. Sutter, D.O., Scott M. Goldman, M.D., John M. Mitchell, B.S., CCP, and Kevin Casey, M.D.: Lankenau Hospital and Medical Research Center, Wynnewood, Pennsylvanis (1993).

Minimally Invasive Mitral Valve Operations: Jose L. Navia, M.D., and Delos M. Cosgrove III, M.D.: Department of Thoracic and Cardiovascular Surgery, The Cleveland Clinic Foundation, Cleveland, Ohio (1996). The Society of Thoracic Surgeons Published by Elsevier Science Inc.

Blood Conservation During Myocardial Revascularization: Delos M. Cosgrove, M.D., Robert L. Thurer, M.D., Bruce W. Lytle, M.D., Carl G. Gill, M.D., Mohan Peter, M.D., and Floyd D. Loop, M.D.: The Annals of Thoracic Surger vol. 28 No. 2 Aug., 1979.

Autotransfusion Following Cardiac Operations: A Randomized, Prospective Study. Robert L. Thurer, M.D., Bruce W. Lytle, M.D., Delos M. Cosgrove, M.D., and Floyd D. Loop, M.D. (1978).

Reoperation for Myocardial Revascularization: Floyd D. Loop, M.D., Robert L. Thurer, M.D., Bruce W. Lytle, M.D., and Delos M. Cosgrove, M.D.: World Journal of Surgery, vol. 2, No. 6 (Nov 1978).

Blood Conservation in Cardiac Surgery: Delos M. Cosgrove, M.D., Floyd D. Loop, M.D., and Bruce W. Lytle, M.D.

Reoperations for myocardial revascularization: The Journal of Thoracic and Cardiovascular Surgery vol. 73, No. 2 (Feb. 1977).

Trial of Roller Pump–Less Cardiopulmonary Bypass System: Manabu Hiroura, Akihiko Usui, M.D., Mitsuo Kawamura, M.D., Mitsuya Murasc, M.D., Michiaki Hibi, M.D., Katsuhiko Yoshida, M.D., Yasuhiro Tomida, M.D., Fumihiko Murakami, M.D., Hideki Ooshima, M.D.: Division of Cardiovascular Surgery, Cardiovascular Center Owari Prefectural Hospital, 2135 Kariyasuga, Ichinomiya, Aichi, 491 Japan: Department of Thoracic Suregery, Bogoya University School of Medicine, 65 Tsurumai. Shouwaku, Nagoya, Aichi, 466 Japan.

\* cited by examiner

CARDIOPULMONARY BYPASS SYSTEM USING VACUUM ASSISTED VENOUS DRAINAGE

TECHNICAL FIELD

The present invention relates generally to a cardiopulmonary bypass system which is useful in connection with minimally invasive cardiovascular surgical procedures, and more specifically, to a cardiopulmonary bypass system having venous drainage which is assisted by a vacuum.

BACKGROUND OF THE INVENTION

Various cardiovascular surgical procedures, including repair or replacement of aortic, mitral and other heart valves, repair of congenital defects, coronary artery bypass grafting, and treatment of aneurysms, involve arrest of cardiac function. In such procedures, a cardiopulmonary bypass ("CPB") system must be used to oxygenate the blood and maintain circulation of the oxygenated blood through the patient during the entire time the heart is arrested. Typically, the components of the CPB system include, in sequence, one or more cannulae which are inserted into one or more major veins, such as the inferior vena cava, or into the heart itself for draining or withdrawing deoxygenated blood from the patient, a reservoir for collecting the venous blood, an oxygenator for removing $CO_2$ from and oxygenating the deoxygenated blood, a filtration unit, an arterial pump for pumping the oxygenated blood back into the patient, and a cannulae which is inserted into a major artery such as the aorta or femoral artery for delivering oxygenated blood to the patient. The components of the CPB system additionally include tubing for carrying the blood throughout the CPB system.

Before the CPB system is connected to the patient, a sterile balanced electrolyte solution is added to the tubing and the reservoir to prime the system and thus prevent the introduction of air into the vascular system of the patient. After the CPB system is connected to the patient, the blood and the electrolyte solution, which are together defined herein as the "perfusate," are pumped into the patient through the arterial cannulae at a flow rate of approximately 0.0 to 7.0 (L/min) to ensure adequate perfusion of the patient's organs during surgery. Otherwise, it is necessary to cool the patient. It is also necessary to remove blood from the patient through the venous cannulae at a similar flow rate, which is comparable to the arterial flow rate to prevent distention of the patient's vascular system. Matching the venous flow rate to the arterial flow rate also helps to maintain the volume of the perfusate.

A number of techniques have also been developed to augment venous drainage and ensure an adequate venous flow rate. The most commonly used technique employs gravity to siphon venous blood from the body. Typically, tubing having a diameter of approximately ½" or ⅜" is used for the venous cannulae and the blood reservoir is placed on or near the floor to maximize the siphon effect. The oxygenator and arterial pump are also placed on or near the floor to minimize the length of tubing used to connect these CPB components to the reservoir. However, a considerable length of tubing, typically about 40 to 80 inches, is still needed to connect the patient to the reservoir and to the arterial pump. Thus, the patient's blood interacts with a large surface area of tubing which increases the possibility of hemodilution, where the tubing is primed, as well as hemolysis.

Moreover, since the priming volume of the electrolyte solution which is provided to the patient is dependent on the length and diameter of the tubing used, the gravity assisted technique requires a large priming volume. In a conventional cardiopulmonary bypass system, over 40% of the priming volume may be used to fill such tubing, which may be as high as 2400 ml of priming volume. High priming volumes may dilute the patient's red blood cells, platelets, and plasma proteins. Such hemodilution may lead to complications during recovery. For example, patients having diluted platelets and plasma proteins may be more likely to suffer from bleeding problems due to inadequate coagulation. Such patients may be more likely to suffer from post-operative anemia and thus require transfusions.

The large diameter venous cannulae that are required for the gravity assisted technique also have the potential to cause difficulties for surgeons using recently developed minimally invasive procedures for the cardiovascular surgery. In such procedures, a small incision, typically 10 cm, is made to gain access to the heart. If venous cannulae having a large diameter are inserted through this incision, the remaining working space available to the surgeon is significantly reduced.

Another technique for augmenting venous drainage uses a centrifugal pump connected to the venous line as described in L. Solomon et al., Augmented Femoral Venous Return, *Ann. Thorac. Surg.* (1993) 55:1262-3. Typically, in this technique, a venous cannulae is inserted into the right femoral vein and then guided to and positioned in the right atrium. The arterial portion of the vascular system is accessed through a cannulae which is inserted into the left femoral artery. Unfortunately, such femoral-femoral cannulation can lead to complications such as thrombophlebitis, wound infections, and dissections.

Moreover, the inclusion of additional centrifugal pumps to the CPB system has disadvantages. For example, such addition increases the amount of tubing required to carry the blood through the system, and thus increases the priming volume of electrolyte solution and contributes to greater hemodilution. Adding centrifugal pumps and increasing tubing used by the CPB system also increases the potential for hemolysis. Finally, including additional pumps also adds to the overall cost of the CPB system.

Thus, it is desirable to have a new CPB system which overcomes the disadvantages of the currently used systems. A CPB system which reduces the required priming volume of electrolyte solution would be especially desirable for cardiovascular surgeries conducted on both adult and pediatric patients. A CPB system which employs venous cannulae having a diameter smaller than those cannulae currently used in the gravity assisted venous drainage technique would also be especially desirable for minimally invasive procedures. A CPB system which eliminates the necessity of positioning the oxygenator and arterial pump a significant distance below the patient would also be desirable, as it would reduce the tubing length and prime. The CPB system which does not require additional, expensive equipment, such as a centrifugal pump, would also be advantageous.

SUMMARY OF THE INVENTION

The present system provides improved vacuum assisted venous drainage in a cardiopulmonary bypass system. The system preferably includes a sealed venous reservoir interconnected with a vacuum regulator subassembly, a valve subassembly, and a vacuum supply. The reservoir is preferably supplied via reduced diameter cannulae, and may be interconnected with either a heart/lung machine, or to a combination of components used in the heart/lung machine, for example, positive pressure pumps, a blood oxygenation unit, a filtration unit and a heat exchange unit. Use of the present system enables numerous advantages over known CPB systems used in both standard and minimally invasive cardiovascular surgical procedures. Using the present system and eliminating the use of a gravity system to provide venous blood flow from the patient results in numerous advantages. Some of the advantages obtained include: decreased size of the holes in the heart from using smaller venous cannulae; reduced venous priming volumes resulting in reduced hemodilution; reduced system tubing requirements resulting in reduced hemolysis; reduced cannulae size while maintaining desired venous flow rates and enabling increased access to the operative field during cardiovascular procedures; reduction in the use of centrifugal or roller pumps previously used for venous flow resulting in reduced hemolysis and reduced system costs; avoiding air locks in the venous drainage line; and increased flexibility in patient positioning and system location in the operating room, since the patient need not be elevated above the reservoir as high as previously required.

Using the present system, venous blood flow from the patient is provided directly to the sealed venous reservoir. Additionally, intermittent cardiotomy blood flow from the vent and suction lines may be provided to the reservoir. The preferred reservoir is a conventional design sealed, hard-shell cardiotomy and venous reservoir. Where an alternate cardiotomy reservoir is provided for the vent and suction lines, the vent and suction ports to the reservoir are occluded with a conventional capping kit to seal the unit. Additional modifications to the reservoir, such as additional sealing, may be required to be made to ensure that adequate sealing is obtained to maintain the reservoir under negative pressure.

The reservoir is interconnected with a conventional heart/lung machine, or, alternatively, positive pressure or roller pumps interconnected with a conventional blood oxygenation unit and heat exchange unit, either or any of which may be used, and are referred to herein as the patient support unit. The patient support unit receives blood pumped from the reservoir for removal of carbon dioxide, addition of oxygen, provides appropriate temperature adjustment, and returns the blood supplied to the patient, preferably directly to the aorta. The heart/lung machine typically includes four roller pumps, one for pumping arterial blood back to the body, one for pumping blood cardioplegia to the body, one for venting additional blood from the patient and one for suctioning blood from the patient. In the embodiment of the present invention where a heart/lung machine or patient support unit is used, four pumps are used. Still further, in the event cardioplegia is not required to be provided to the patient via the patient support unit, only three pumps are used. In a still further embodiment, only three of the four pumps are used if the vent and suction functions are performed by interconnecting the vent and suction lines with the vacuum supply to supply such blood from the patient to the reservoir. It is noted that one of the main advantages of the present device is that the venous lines from the patient to the reservoir need not be primed. This reduced priming volume results in the use of less than 1 liter, or between 1200 and 975 cc, of prime in the remainder of the system, depending on the type of surgery being performed.

A vacuum source or supply is interconnected with the reservoir to apply a negative pressure or vacuum to the system. The vacuum source used is a conventional house or wall vacuum supply, having a constant pressure of −24 kpas or −450 mmHg. However, it should be understood that any vacuum supply may be used as a source for the system. A conventional negative pressure monitor is provided at a venous entry port to the reservoir to constantly monitor the negative pressure within the reservoir. The preferred negative pressure measured at the reservoir entry port of the present system is approximately −25 to −70 mmHg. It will be understood by those of ordinary skill in the art that during a cardiopulmonary bypass procedure it is the rate of venous blood flow through the system which is monitored, and not the venous blood pressure levels, since the goal of the CPB system is to reduce the pressure as low as possible, while continuing to maintain adequate blood flow to and from the patient via the system.

Intermediate the venous reservoir and the vacuum supply, a regulator subassembly and valve subassembly are provided. The reservoir is interconnected with the subassemblies via a short length, approximately 12 inches, of ¼ inch sterile tubing. The regulator subassembly includes a vacuum gauge to monitor the negative pressure supplied to the system, and a vacuum regulator, having a delivery gauge, enabling increasing or decreasing adjustment of the pressure level as may be required during the surgery to maintain desired blood flow from and to the patient. A manifold is connected between the vacuum gauge and the vacuum regulator to ensure supply of the desired vacuum level upon adjustment. The vacuum regulator is preferably preset prior to the surgery procedure at the estimated desired pressure level. The desired vacuum level is estimated based upon numerous patient characteristics and surgery factors, such as size of the patient, the procedure being performed, the cannulae being used, etc. The vacuum regulator includes an "on/off" valve, so that when it is desired to initiate the venous drainage, the vacuum regulator may simply be moved from the "off" position to the "on" position. The regulator subassembly and manifold may be bracketed to the pump hardware of the patient support unit.

The valve subassembly of the present system preferably includes a vacuum relief valve, vacuum relief controls, a high negative pressure relief valve and first and second water vapor relief traps. The reservoir is interconnected with the vacuum relief controls to enable a quick disconnect of the negative pressure if the suction increases too rapidly, or other conditions require termination of the vacuum. In the preferred embodiment, the vacuum relief controls comprise an open tube extending from the tubing interconnecting the reservoir and the vacuum regulator, which is clamped to a closed condition during operation using surgical tubing clamps, or other conventional clamping means. In the clamped or closed condition, the system operates under the desired negative pressure level. However, release of the clamped condition opens the system to atmosphere to remove any negative pressure.

Once the patient is prepared, following heparinization, the bypass may be initiated. After confirming the preset desired negative pressure on the pressure regulator, the vacuum relief controls are clamped closed, and the vacuum regulator is moved to the "on" position. An arterial pump of the patient support unit is then activated. The vacuum levels are confirmed on the negative pressure monitor, and the system vacuum levels are confirmed using the vacuum gauge and delivery gauge. The application of the desired negative pressure to the system immediately, and without priming of the venous lines, provides venous blood flow to the reservoir.

Preferably, the improved system makes use of cannulae having a reduced diameter over those used in conventional cardiovascular surgery and CPB systems. The reduced diameter cannulae, approximately 20F to 28F, are preferably inserted directly into the right atrium of the heart, or to the vena cava. It should be understood that in pediatric surgeries cannulae having diameters as small as 18F are also used.

The flow rates for venous drainage using the present system are preferably in the range of 0.0 to 7.0 L/min, depending on the procedure used. Thus, it will be apparent to one of ordinary skill in the art that the present system obtains conventional CPB blood flow rates, while at the same time providing numerous other advantages over the prior systems which make use of expensive positive pressure pumps and/or require increased priming volumes, while still obtaining the desired reduced cannulae diameters.

Because the present system does not rely solely on gravity for venous drainage, the system does not require increasing the distance of the patient from the floor during use, nor must the system be located on the floor. The system is preferably located near the patient support unit, but may be positioned as desired by the surgical team. For example, the reservoir, regulator and valve subassemblies may be supported on brackets extending from the patient support unit, or they may extend from, and be movable with, the surgical table supporting the patient, and thus be moved with the patient, particularly where a heart/lung machine is not used and a modified combination of pumps and heat exchangers, as set forth herein, are used. Such positioning provides increased flexibility for the surgery team during a procedure.

It should be understood that the present system may be useful, not only in connection with minimally invasive cardiovascular surgery, but with any surgical procedure using the CPB system. A further understanding of the nature and advantages of the invention may be realized by reference to the following description of the drawings, specification and claims.

DETAILED DESCRIPTION OF THE PREFERRED EMBODIMENT

Figure 1:
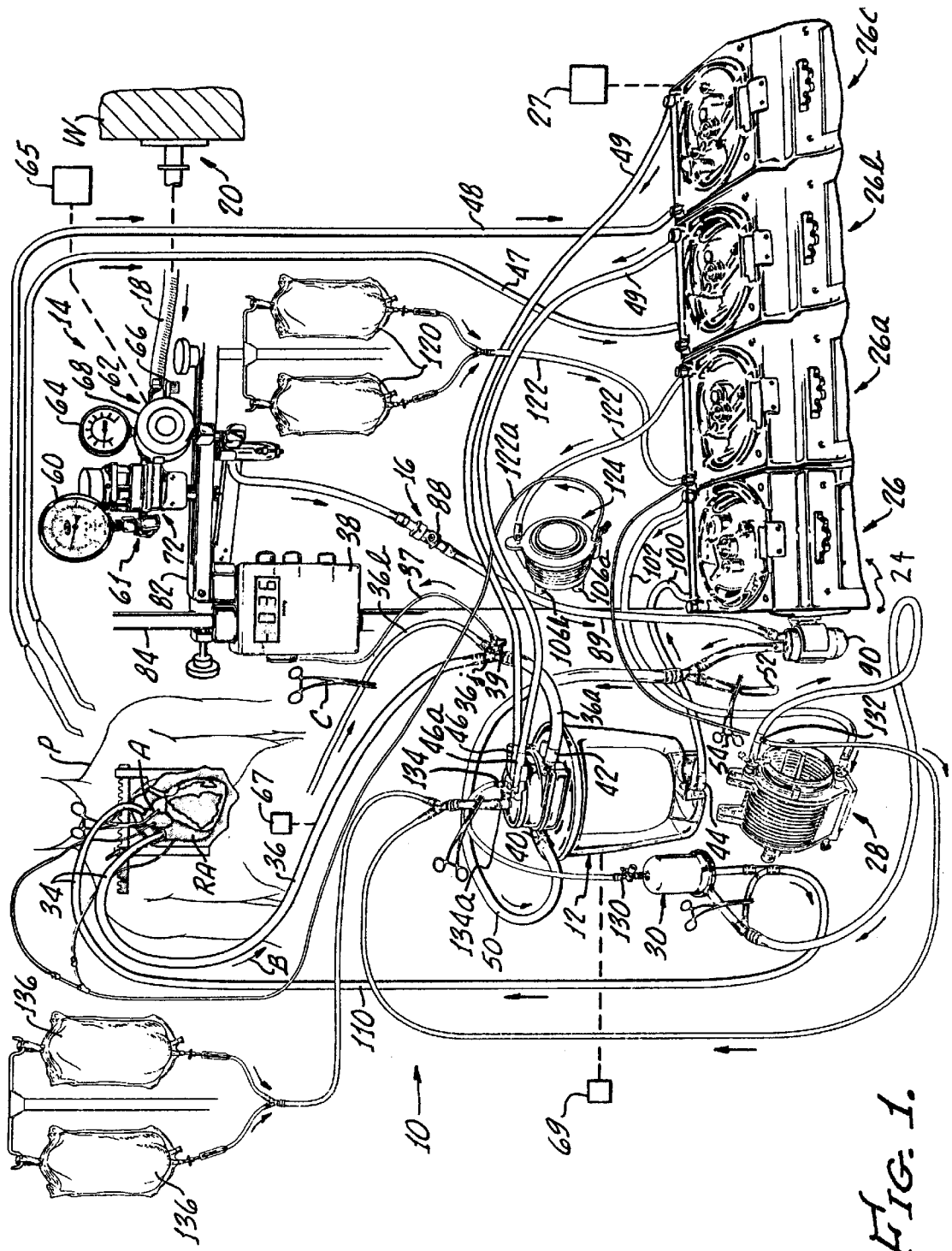
FIG. 1 is a schematic illustration of a cardiopulmonary by-pass system with the vacuum assisted venous drainage system of the present application.

The present vacuum assisted venous drainage system used in a cardiopulmonary by-pass system, generally illustrated in FIG. 1, bears reference numeral 10. The present system preferably includes a sealed reservoir 12, interconnected with a vacuum regulator subassembly 14, a valve subassembly 16, and a vacuum supply line 18 interconnected with a vacuum wall source 20. The reservoir 12 is preferably supplied with blood flow from the patient P via reduced diameter cannulae, and may be interconnected with either a heart/lung machine 24, partially illustrated in FIG. 1, or to a combination of components used in the heart/lung machine, such as roller pumps 26, 26a, 26b, 26c a blood oxygenation and heat exchange unit 28 and a filtration unit 30. It will be understood by one of ordinary skill in the art that each of these components is conventional, and readily available from numerous well known sources.

The improved system preferably uses cannulae having diameters of approximately 20F to 28F, but it is anticipated that even smaller diameters may be used. As schematically illustrated, these are either inserted directly into the right atrium RA of the heart, as shown in FIG. 1, to the vena cava, or may alternatively be inserted as desired. The cannulae are conventional single stage venous cannulae, available, for example, from Medtronic DLP, Inc. of Grand Rapids, Mich. The cannulae 34 are interconnected with conventional ⅜ inch surgical tubing 36, which is interconnected with an inlet port of the reservoir 12. In the preferred embodiment, the reservoir 12 is an HSR-4000 Gold hard-shelled venous reservoir which is closed to the atmosphere and has a fixed volume, or is not flexible. The reservoir is available, for example, from Baxter Healthcare Corporation, Bentley Division, of Irvine, Calif.

The reservoir 12 includes various inlet and outlet ports described as follows: vacuum inlet 40 indirectly connected to the vacuum supply line 18 and vacuum wall source 20 which supplies a vacuum to the reservoir; a venous blood inlet 42 which supplies venous blood flow from the patient via tubing 36, 36a; and a blood outlet 44 which supplies blood from the reservoir to the blood oxygenation and heat exchange unit 28, the blood filtration unit 30 and the patient P, using the roller pump 26. An additional optional venous blood supply line may also be provided, but is not illustrated in use in FIG. 1, as a clamp C is provided on tubing 36b. The additional cardiotomy blood inlets 46, 46a may also be used, as in the illustrated embodiment, but may also be sealed using conventional caps or plugs in these connectors. In the alternate embodiment of FIG. 5, cardiotomy blood inlet 46' may be used to supply cardiotomy blood via vent line 47' and suction line 48' to be combined with the venous blood supply of the reservoir 12'. The vent and suction lines 47, 48 are manually operated by the surgical staff to remove blood from the patient P.

It is noted that where similar or duplicate elements are referred to they will be referred to with an additional alphanumeric designation, and where they are present in an alternate embodiment of the present system, the elements will be referred to with a prime designation. In either case, duplicate elements will not be described in further detail to the extent their performance is substantially similar to the embodiments previously described. For example, the roller pumps illustrated in FIG. 1 will be referred to as 26, 26a, 26b, etc., and in FIG. 5 as 26', 26a', 26b', etc.

To confirm the vacuum level within the reservoir, negative pressure is monitored prior to entry of blood into the reservoir 12. The conventional negative pressure monitor 38, for example, a digital Series 60000 pressure display monitor available from Medtronic DLP, Inc. of Grand Rapids, Michigan, is positioned to receive blood via tubing 37 from an interconnecting joint 36j intermediate tubing 36 and tubing 36a. A conventional Luer port 39 is also provided at this interconnection so that blood samples may be withdrawn if desired. The preferred negative pressure of blood, which is continuously measured at this point within the system, is approximately −25 to −70 mmHg.

As seen in FIG. 1, the vacuum inlet connection 40 to the reservoir 12 is interconnected with a reservoir supply line 50, which is indirectly connected with the vacuum wall source 20. This series of interconnections provides a vacuum to the reservoir, to place the reservoir under negative pressure and enable drainage of venous blood from the patient P through the system. In the preferred embodiment, the vacuum wall source 20 used is the conventionally available source of vacuum supplied to many, if not all U.S., surgical rooms. As previously described, the wall source supplies a vacuum at a constant pressure of approximately −450 mmHg. Attached to the wall source 20 via a conventional fastener, is the vacuum supply line 18.

Figure 3:
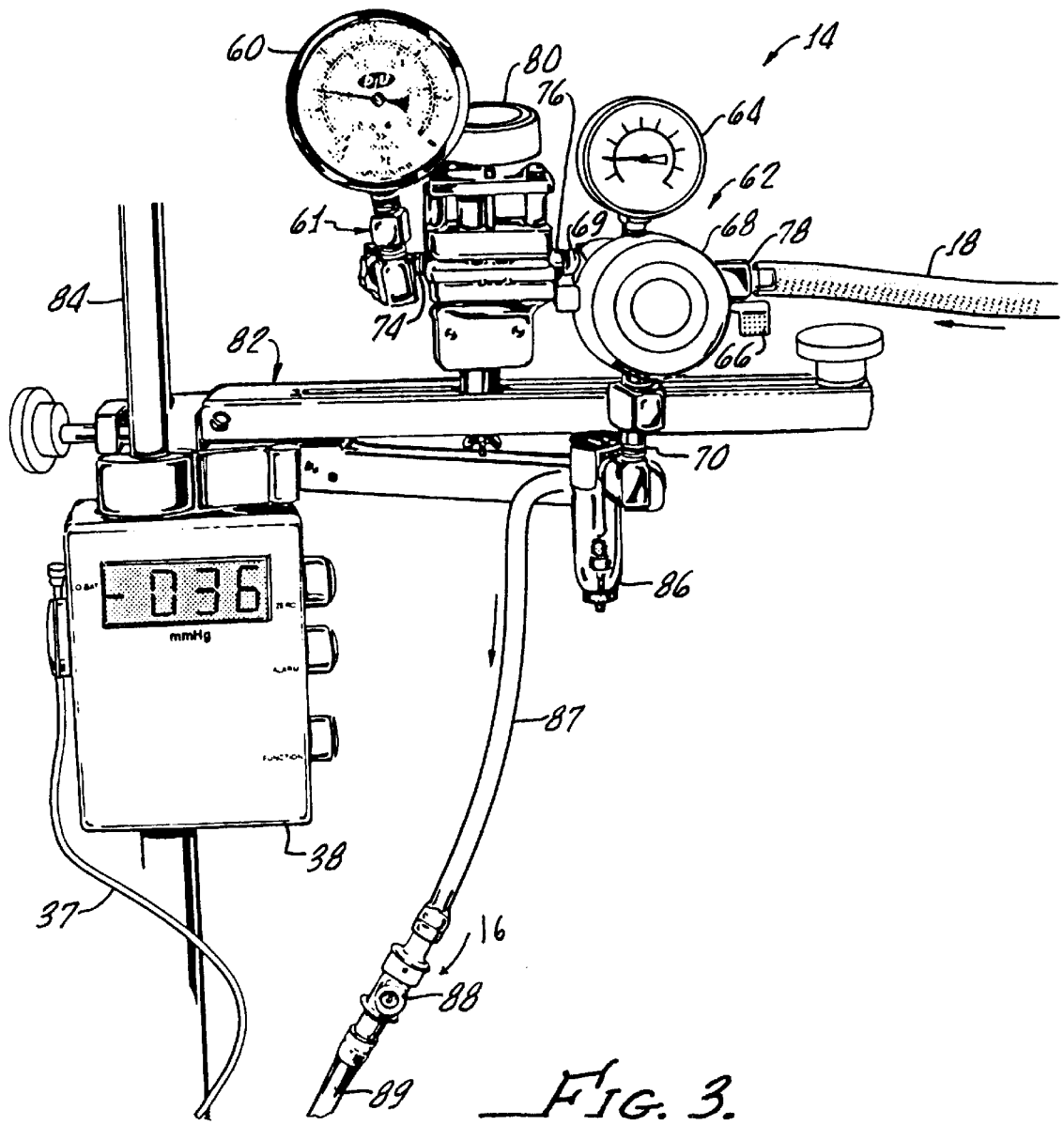
FIG. 3 is a schematic illustration of the vacuum regulator and valve subassemblies of FIG. 1.
Figure 4:
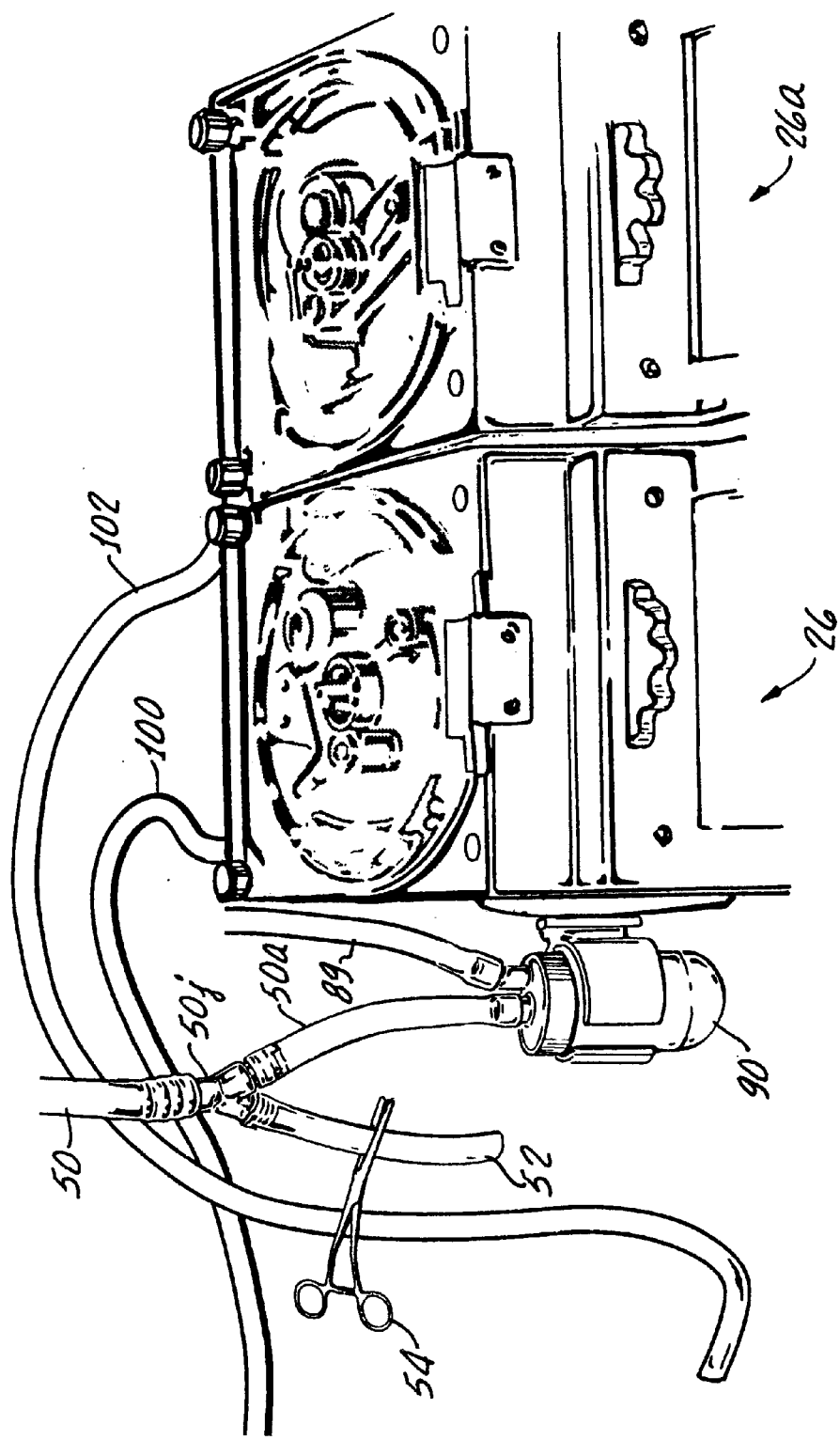
FIG. 4 is a schematic illustration of the valve subassemblies and roller pumps of FIG. 1.

Intermediate the reservoir supply line 50 and the vacuum supply line 18, a vacuum regulator subassembly 14 and valve subassembly 16 are provided. The regulator subassembly 14 includes a vacuum gauge 60 and a vacuum regulator 62. The vacuum gauge 60 is used to monitor the negative pressure level of the system, and is preferably a conventional Duro-United vacuum gauge, with an inlet port 61. The vacuum regulator 62, has a delivery gauge 64 with an on/off lever 66, and an adjustment knob 68 to enable increasing and/or decreasing adjustment of the pressure level as desired. As shown in FIG. 3, the vacuum regulator is a conventional general purpose suction regulator available from Nellcor Puritan-Bennett Co., having a first inlet port 69 and a second outlet port 70.

A manifold 72 is interconnected between the vacuum gauge inlet port 61, the vacuum regulator first inlet port 69 and the vacuum supply line 18. In the illustrated embodiment of FIG. 3, the manifold 72 is a section of hollow steel tubing with first, second and third ports 74, 76, 78, respectively. A threaded interconnection connects the manifold 72 with the inlet port 61 of the vacuum gauge 60 at the first port 74, the first inlet port 69 of the vacuum regulator 62 at the second port 76 and a friction fit engagement with the vacuum supply line 18 at the third port 78. Using this arrangement, the manifold 72 is continuously supplied with negative pressure via the supply line 18. The manifold 72 supplies the vacuum gauge 60 and the vacuum regulator 62. The vacuum gauge 60 provides a reading of the negative pressure level within the system emanating from the wall source 20. Through the vacuum regulator 62, the present system is supplied with negative pressure at the level set using the adjustment knob 68 and the on/off lever 66. In the illustrated embodiment of FIG. 3, the manifold 72 is shown clamped within a conventional adjustable support clamp 80. The support clamp is itself clamped within a conventional adjustable horizontal clamp 82. The horizontal clamp 82 is engaged along a vertical pole 84 which is secured to the surgery room floor or other fixed equipment. The vertical pole 84 likewise adjustably supports the negative pressure monitor 38.

The reservoir 12 and reservoir supply line 60 are indirectly supplied with negative pressure via the second port 70 of the vacuum regulator 62. Intermediate the vacuum regulator 62 and the reservoir supply line 60 is a conventional vapor trap 86. The vapor trap 86 protects the regulator subassembly from damage due to vapor return from the direction of the reservoir supply line 60.

Figure 2:
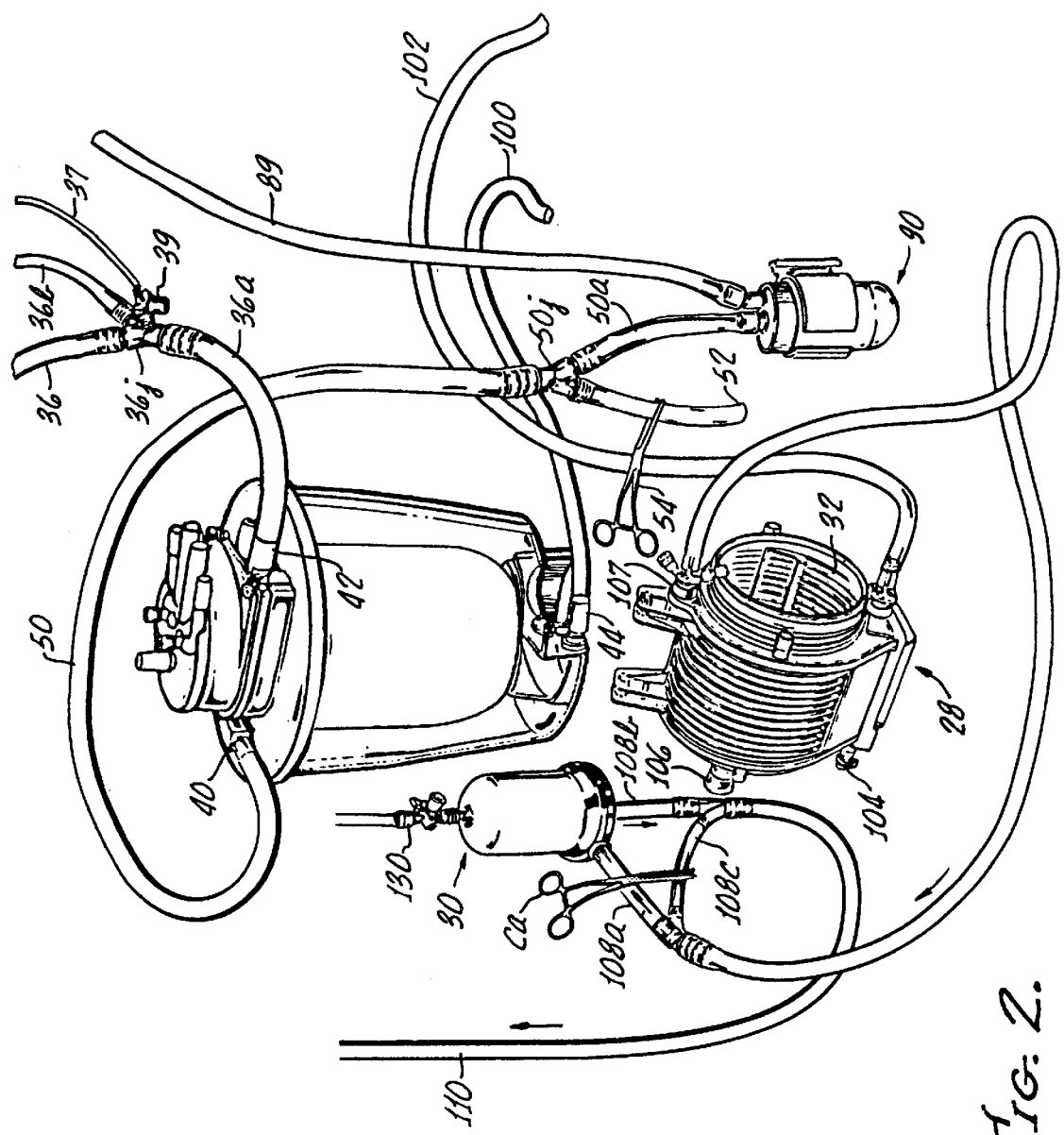
FIG. 2 is a schematic illustration of portions of the vacuum line, reservoir, oxygenation unit, filtration unit of FIG. 1.

As seen in FIGS. 1 and 2, the valve subassembly 16 is positioned intermediate the regulator subassembly 14 and the reservoir 12. The valve subassembly 16 includes a conventional check valve 88, which is supplied with negative pressure from the vapor trap 86 via tubing 87. The check valve 88 serves as a safety relief valve, which, when the system negative pressure level reaches −80 mmHG, the valve operates to let in room air. A still further vapor trap 90 is provided for protection of the vacuum regulator subassembly 14 which is interconnected with the check valve 88 via tubing 89. The trap 90 may be supported on the roller pump 26, as illustrated, or on other available support structure. From the vapor trap 90, negative pressure is supplied via the vacuum inlet 40 to the reservoir 12 via tubing 50a and through an interconnecting joint 50j intermediate tubing 50a and tubing 50. A manual system disable line 52 also extends from the interconnecting joint 50j. The line 52 is conventional tubing secured with a surgical clamp 54. When the system is in "on" condition, supplying negative pressure to the reservoir 12 for drainage of venous blood from the patient P, the clamp 54 is clamped on the tubing 52 as shown in FIG. 2. When the clamp 54 is removed, the system 10 is open to atmosphere, and no vacuum is provided through the system. This manual system disable line 52 provides a convenient "on" to enable the system, as well as an immediate shut off for the system, should this become necessary during system operation.

Prior to operation of the system, the adjustment knob 68 of the vacuum regulator 62 is used to preset the estimated desired vacuum level. The desired vacuum level is estimated based upon numerous patient characteristics and surgery factors, such as size of the patient, the procedure being performed, the cannulae being used, etc., which are well known to those of ordinary skill in the art, and range between −25 and −70 mmHG. Once the patient is prepared, the heart/lung machine 24, or the arterial pump 26 component of the patient support unit, is then activated. Likewise, the cardioplegia supply pump 26a may be activated when it is desired to supply the patient P with additional blood/fluid components. The vent pump 26b and suction pump 26c may also be activated to remove blood from the patient P as desired.

As shown in FIG. 1, cardioplegia fluid is supplied to the cardioplegia supply pump 26a from one or more supply bags 120 (containing either blood or other fluids) via tubing 122. Activation of the pump 26a enables the supply of cardioplegia fluid mixed by the pump 26a through a heat exchange unit 124 having a heating/cooling port inlet 106a, and a port outlet 106b. The unit 124 is supplied with hot or cold fluid, typically water, depending on the temperature change desired, via the port inlet 106a, which fluid is removed via the port outlet 106b. Following appropriate heating or cooling, the cardioplegia fluid is pumped via tubing -122a to the patient P as indicated. The activation of the vent pump 26b and/or suction pump 26c, removes blood from the patient via the hand held devices illustrated, or other conventional mechanisms, to the vent line 47 or suction line 48, respectively. The roller pumps 26b, 26c, supply the removed blood to the cardiotomy blood inlets 46a, 46, respectively, via tubing 49, for combination with the direct venous blood flow to the reservoir 12.

Turning again to the further operation of the system 10, when the vacuum regulator "on/off" lever 66 is in the "on" position, and the manual system disable line 52 is clamped in the closed condition, the system is supplied with negative pressure and venous drainage to the reservoir 12 immediately commences without requiring priming of any of the lines 36, 36a. The application of the desired negative pressure to the system immediately, and without priming of the venous lines, provides venous blood flow to the reservoir 12. The system vacuum levels are confirmed on the negative pressure monitor 38, vacuum gauge 60 and delivery gauge 64.

The venous blood flow B supplied to the filtered reservoir 12 is returned to the patient P via pump 26 of the patient support unit or heart/lung machine 24, as previously described. In the illustrated embodiment of FIGS. 1 and 5, blood exits the reservoir 12, 12' through the blood outlet 44, 44' to, and using, the roller pump 26, 26' and tubing 100, 100'. The blood is then pumped in the direction of the arrows illustrated, via tubing 102, to the oxygenation and heat exchange unit 28 for removal of $CO_2$ and the addition of oxygen. The unit 28 is of a conventional design, with a gas exhaust 104 for $CO_2$ output, and a gas inlet (not illustrated, but positioned adjacent the gas exhaust 104) for oxygen input. The unit 28 is a conventional device having a stainless steel support structure 32. The unit 28 is supplied with hot or cold water, depending on the temperature change desired, via heating/coolant inlet port 106, and outlet port 106a (not illustrated). As with the cardioplegia heat exchange unit 124, the hot or cold fluid is provided to the inlet port 106 at a rate of approximately 20 l/min, for appropriate temperature adjustment of the blood or fluid between 10°–37° C. The warmed blood B is then returned to the patient P via outlet 107 and tubing 108, 108a, 108b through the filtration unit 30. Tubing 110 supplies the filtered blood directly to the aorta A via reduced diameter cannulae 34, as illustrated in FIG. 2. The filtration unit 30 is conventionally available, and provides a filter of 20 $\mu$ for blood passing therethrough. A prime port 130 permits the return of blood, as well as vapor, to the reservoir via prime inlets to the reservoir 134, 134a. The present system provides return blood flow to the patient at approximately 7 l/min. In the event additional blood flow is required, or filtration is not required, blood flow may be provided to tubing 110 for direct return to the patient via tubing 108c. The surgical clamp Ca is manually used to determine the desired flow pattern. As further noted in FIG. 1, that conventional prime ports 130, 132 may be provided from the filtration unit 30 and oxygenation and heat exchange unit 28, respectively, to prime inlets 134, 134a in the reservoir 12 via the tubing indicated. The priming fluid may be provided from supply bags 136 via the tubing as indicated in FIG. 1. As shown in FIG. 1, conventional priming of the filtration and oxygenation and heat exchange units may be clamped or valved to prevent or permit flow as may be desired. The availability of such return lines to the reservoir 12 permits recirculation of blood flow during use of the system as may be required.

Figure 5:
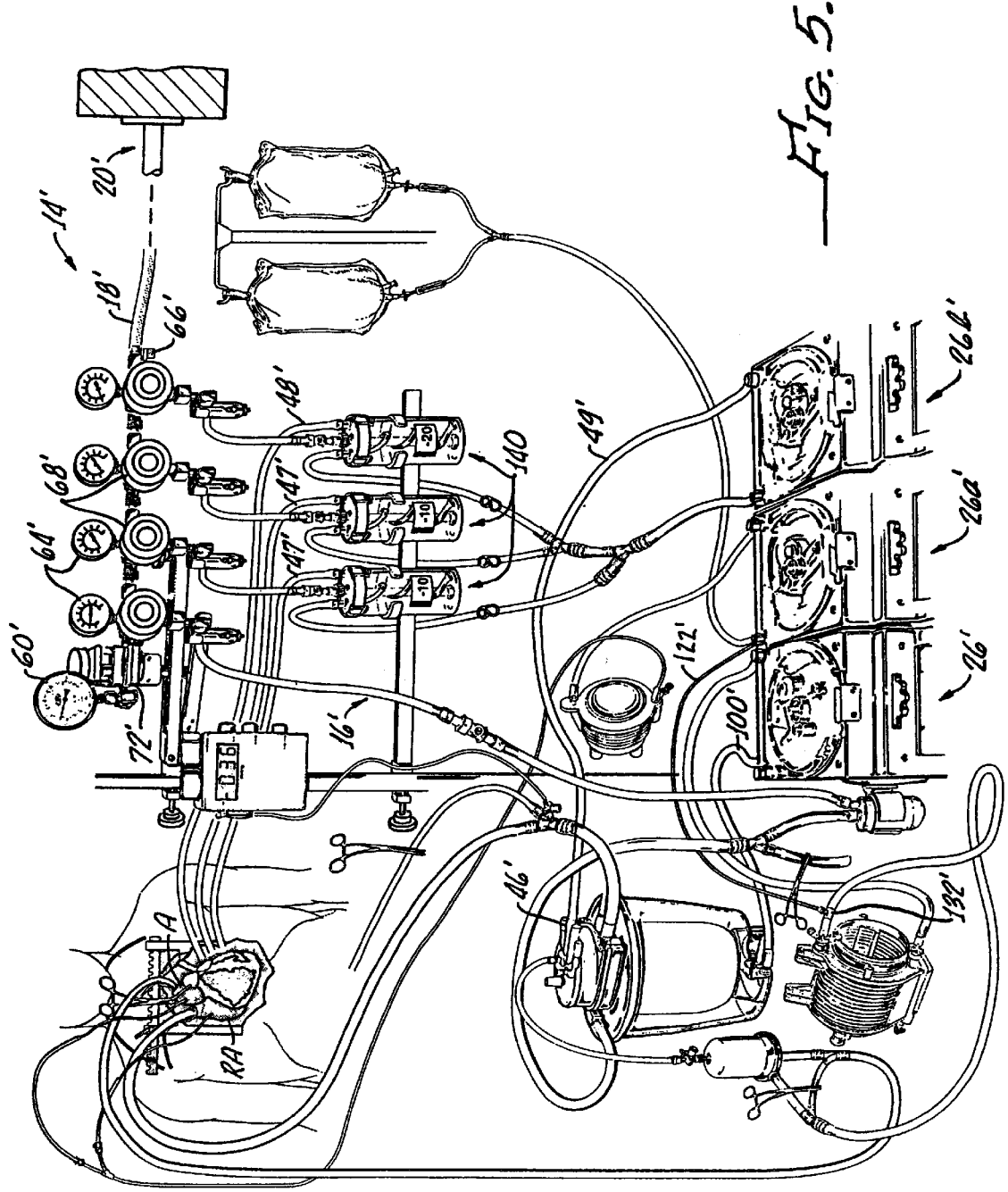
FIG. 5 is a schematic illustration of an alternate embodiment of the vacuum assisted venous drainage system.
Figure 6:
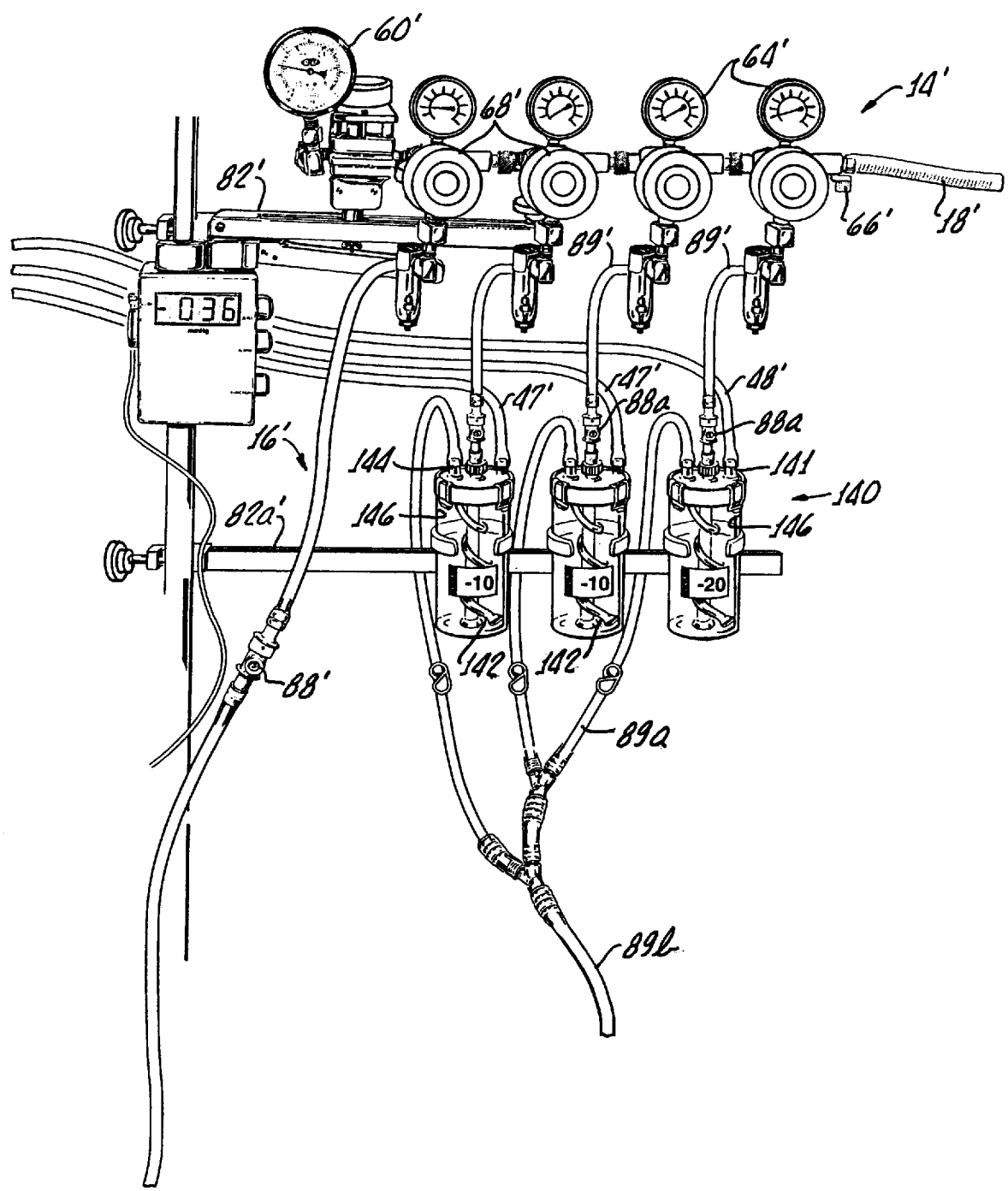
FIG. 6 is a schematic illustration of the vent and suction reservoir subassemblies of the embodiment of FIG. 5.

In the embodiments of FIGS. 1–4, it should be understood that four roller pumps 26, 26a, 26b, 26c are used, as blood from the vent line 47 and suction line 48 is removed from the patient using the positive pressure of roller pumps 26b and 26c, respectively. In the embodiment of FIG. 5 of the present system only three pumps are used. The operation of two vent and suction pumps are combined in one pump 26c' to supply blood pumped from the patient to the reservoir 12'. As shown in FIG. 5, the present vacuum assist system is used to indirectly connect a single or multiple vent and/or suction tubing lines supplying blood from the patient P to the pump 26c', under a vacuum. It will be understood by one of ordinary skill that any number of vent lines may be used in the present system, as are desired or not, during operation of the system. As illustrated in the preferred embodiment of FIGS. 5 and 6, each of the vent and suction tubing lines 47', 48', respectively, supply blood from the patient to an intermediate reservoir subassembly 140, supported on an adjustable bracket 82a. The intermediate reservoir subassemblies 140 are under a predetermined desired negative pressure as illustrated, which is −10 mmHg for the vent lines, and −20 mmHg for the suction lines. As illustrated in FIGS. 5 and 6, between each of the intermediate reservoir subassemblies 140 and the vacuum wall source 20' are elements of the vacuum regulator subassembly 14' substantially as previously described and illustrated. A vacuum gauge 60' monitors system vacuum levels, and individual vacuum regulators 62' for each vacuum line are provided to adjust the negative pressure level as needed. The manifold 72' interconnects each of the respective regulators 62' and the gauge 60'. Vapor traps 86' are additionally used adjacent each of the regulators 62' to protect the regulators from vapor damage.

In addition to the valve subassembly 16' components which are similar to those in FIG. 1, the FIG. 5 embodiment includes additional check valves 88a positioned between the vapor traps and the intermediate reservoir subassemblies 140 to prevent high negative pressure as previously described. Each of the intermediate reservoirs 140 is a hard shelled, sealed unit, preferably including a replaceable liner or bag 146. Due to the use of such liners, the intermediate reservoirs are preferably reusable. As illustrated, once cardiotomy blood is supplied from the vent and suction lines to an inlet 141 of the intermediate reservoir subassemblies 140 under a vacuum, it is removed for providing to the reservoir 12' via the transfer or positive pressure roller pump 26c'. The blood is removed from each of the intermediate reservoirs 140 via reservoir tubing 142 to an outlet 144, which is interconnected with tubing 89a, and by the interconnection illustrated, with tubing 89b.

Other differences illustrated in the embodiment of FIG. 5 include the elimination of priming lines to the reservoir 12', as well as the connection of the prime port 132' from the oxygenation and heat exchange unit 28' directly to the input of the cardioplegia pump 26a', at tubing 122', for mixing by the pump 26a'.

Flow rates for venous blood flow both to and from the system using the embodiments illustrated and described are preferably in the range of 0.1 to 7.0 L/min, depending on the procedure used. It should be understood by one of ordinary skill in the art that various modifications to the details of construction, use and operation of the embodiments of the present system may be made, all of which are within the spirit and scope of the following claims.

We claim:

1. An adult sized minimally invasive cardiopulmonary bypass system for utilizing negative pressure to enhance venous drainage to a venous drainage reservoir, comprising:

a source of vacuum;

a venous cannula suitable for minimally invasive surgical applications and being sized no greater than 28 French;

a manifold in fluid communication with the source of vacuum;

a pressure regulator in fluid communication with the manifold to receive negative pressure from the source of vacuum;

a hard-shelled venous reservoir sealed to the atmosphere and having a venous blood inlet port, a blood outlet port, and a vacuum inlet port;

first tubing connecting the pressure regulator to the vacuum inlet port of the reservoir to transmit negative pressure to the sealed reservoir;

second tubing connecting the venous cannula to the venous blood inlet port of the reservoir to transmit negative pressure from the reservoir to the venous cannula;

a first pressure sensor and monitor connected to the second tubing for measuring and displaying the negative pressure of the blood in the second tubing prior to entry into the reservoir;

a second pressure sensor and monitor in fluid communication with the manifold to receive negative pressure from the source of vacuum for measuring and displaying the magnitude of negative pressure from the source of vacuum;

a negative pressure adjustment control in fluid communication with the manifold and the pressure regulator for adjusting the pressure within the reservoir;

a check valve in fluid communication with the interior of the reservoir and configured to permit atmospheric air to enter the reservoir when the pressure in the reservoir falls below a threshold pressure; and, a vapor trap positioned in the first tubing.

2. The system of claim 1, wherein the check valve is positioned in the first tubing and wherein the first vapor trap is located in the first tubing between the check valve and the regulator and further including a second vapor trap positioned in the first tubing between the check valve and the reservoir.

3. An adult sized minimally invasive cardiopulmonary bypass system for utilizing negative pressure to enhance venous drainage to a venous drainage reservoir, comprising:

a source of vacuum;

a venous cannula;

a manifold in fluid communication with the source of vacuum;

a pressure regulator in fluid communication with the manifold to receive negative pressure from the source of vacuum;

a hard-shelled venous reservoir sealed to the atmosphere and having a venous blood inlet port, a blood outlet port, and a vacuum inlet port;

first tubing connecting the pressure regulator to the vacuum inlet port of the reservoir to transmit negative pressure to the sealed reservoir;

second tubing connecting the venous cannula to the venous blood inlet port of the reservoir to transmit negative pressure from the reservoir to the venous cannula;

a first pressure sensor and monitor connected to the second tubing for measuring and displaying the negative pressure of the blood in the second tubing prior to entry into the reservoir;

a second pressure sensor and monitor in fluid communication with the manifold to receive negative pressure from the source of vacuum for measuring and displaying the magnitude of negative pressure from the source of vacuum;

a negative pressure adjustment control in fluid communication with the manifold and the pressure regulator for adjusting the pressure within the reservoir;

a check valve in fluid communication with the interior of the reservoir and configured to permit atmospheric air to enter the reservoir when the pressure in the reservoir falls below a threshold pressure;

a vacuum on/off valve provided in the first tubing for alternately enabling and disabling vacuum pressure supplied to the reservoir; and, a first vapor trap positioned in the first tubing.

4. The system of claim 3, further including a second vapor trap positioned in the second tubing.

* * * * *